US009895522B2

(12) United States Patent
Yori (10) Patent No.: US 9,895,522 B2
(45) Date of Patent: Feb. 20, 2018

(54) CELL CULTURE TRANSFERRING INSTRUMENT (71) Applicant: TERUMO KABUSHIKI KAISHA, Shibuya-ku (JP)

(72) Inventor: Kouichirou Yori, Ashigarakami-gun (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 773 days.

(21) Appl. No.: 14/309,112

(22) Filed: Jun. 19, 2014

(65) Prior Publication Data
US 2014/0303598 A1 Oct. 9, 2014

Related U.S. Application Data (63) Continuation of application No. PCT/JP2012/080566, filed on Nov. 27, 2012.

(30) Foreign Application Priority Data

Dec. 20, 2011 (JP) .................................. 2011-277853

(51) Int. Cl.
*A61M 37/00* (2006.01)
*A61F 2/02* (2006.01)
(Continued)

(52) U.S. Cl.
CPC ............ *A61M 37/0069* (2013.01); *A61F 2/02* (2013.01); *C12M 23/26* (2013.01); *C12M 23/54* (2013.01);
(Continued)

(58) Field of Classification Search
CPC ...... C12M 23/26; C12M 23/54; C12M 25/02; C12M 33/02; A61B 10/00; A61B 10/02
(Continued)

(56) References Cited

U.S. PATENT DOCUMENTS 3,800,781 A * 4/1974 Zalucki ................. A61B 10/02
600/562
4,710,192 A * 12/1987 Liotta .................... A61B 17/12
604/907
(Continued)

FOREIGN PATENT DOCUMENTS

EP 0557964 A1 9/1993
JP 9-501065 A 2/1997
(Continued)

OTHER PUBLICATIONS

Extended Search Report dated Jul. 9, 2015 by the European Patent Office, in corresponding European Patent Application No. 12860052.5 (3 pages).
(Continued)

*Primary Examiner* — Edelmira Bosques
(74) *Attorney, Agent, or Firm* — Buchanan Ingersoll & Rooney PC (57) ABSTRACT

A cell culture transferring instrument includes a cylindrical body held by an operator not shown in the drawing, a plunger inserted through the interior of the cylindrical body, a plurality of support members connected to a distal end of the plunger, and an adsorbent capable of adsorbing a sheet-shaped cell culture held by the support members. The support members in contact with the distal end of the cylindrical body are elastically deformed by displacing the plunger toward the proximal end side with respect to the cylindrical body in a state in which the sheet-shaped cell culture is adsorbed to the adsorbent, whereby the adsorbent and the sheet-shaped cell culture are deformed and housed in a housing hole in the cylindrical body.

5 Claims, 5 Drawing Sheets (51) Int. Cl.
  *C12M 1/00* (2006.01)
  *C12M 1/12* (2006.01)
  *C12M 3/00* (2006.01)
  *C12M 1/30* (2006.01)

(52) U.S. Cl.
  CPC ............ *C12M 25/02* (2013.01); *C12M 33/02* (2013.01); *A61M 2202/0007* (2013.01); *A61M 2202/09* (2013.01)

(58) Field of Classification Search
  USPC ........................................................ 604/522
  See application file for complete search history.

(56) References Cited

U.S. PATENT DOCUMENTS

| | | | |
|---|---|---|---|
| 5,817,075 | A | 10/1998 | Giungo |
| 7,985,197 | B2 | 7/2011 | Maeda et al. |
| 2006/0063252 | A1 | 3/2006 | Ito et al. |
| 2010/0106057 | A1* | 4/2010 | Harvey ................ B01L 3/5023 600/573 |

FOREIGN PATENT DOCUMENTS

| | | | |
|---|---|---|---|
| JP | 2005-176812 | A | 7/2005 |
| JP | 2007-229251 | A | 9/2007 |
| JP | 2008-173333 | A | 7/2008 |
| JP | 2009-511 | A | 1/2009 |
| JP | 2010-75081 | A | 4/2010 |
| JP | 4569971 | B2 | 10/2010 |
| WO | WO 2004/083416 | A1 | 9/2004 |

OTHER PUBLICATIONS

International Search Report (PCT/ISA/210) dated Jan. 29, 2013, by the Japanese Patent Office as the International Searching Authority for International Application No. PCT/JP2012/080566.

Hannachi et al., "Fabrication of transferable micropatterned-co-cultured cell sheets with microcontact printing", Biomaterials, Jul. 2009, vol. 30, pp. 5427-5423.

Asakawa et al., "Pre-vascularization of in vitro three-dimensional tissues created by cell sheet engineering", Biomaterials, Feb. 2010, vol. 31, pp. 3903-3909.

* cited by examiner

FIG. 3

CELL CULTURE TRANSFERRING INSTRUMENT

CROSS REFERENCES TO RELATED APPLICATIONS

This application is a continuation of International Application No. PCT/JP2012/080566 filed on Nov. 27, 2012, and claims priority to Japanese Application No. 2011-277853 filed on Dec. 20, 2011, the entire content of both of which is incorporated herein by reference.

TECHNICAL FIELD

The present application relates to a cell culture transferring instrument capable of transferring a sheet-shaped cell culture to a desired position for use in therapy.

BACKGROUND ART

In recent years, in therapy of myocardial infarction and the like, there has been widely known a therapeutic method in which a sheet-shaped cell culture obtained by cultivating and organizing the patient's own cells is transplanted to the affected part. Such a sheet-shaped cell culture is thin film shaped and is therefore fragile. In addition, it is highly liable to stick to itself because of its water content. Accordingly, a skillful maneuver is needed to take the sheet-like cell culture out of the culture dish and transfer it to the affected part or into another container.

In order to transfer such a sheet-shaped cell culture, therefore, a transferring instrument is used. For instance, Japanese Patent No. 4569971 discloses such a transferring instrument, wherein a sheet supporting member which can be freely curved and can adsorb a cell sheet is provided inside a cylindrical housing pipe so as to be movable back and forth. The sheet supporting member is housed inside the housing pipe in a cylindrically deformed state. After being moved to the outside of the housing pipe, the sheet supporting member is unfolded into a planar shape by a pneumatic pressure supplied from an actuator, and adsorbs the cell sheet. In addition, by varying the pneumatic pressure in the state where the cell sheet is adsorbed on the sheet supporting member, the sheet supporting member with the cell sheet adsorbed thereon is curved and deformed into a hollow cylindrical shape, and is moved toward the housing pipe, to be housed inside the housing pipe.

SUMMARY

In the aforementioned transferring instrument, however, it is necessary to bring the sheet supporting member close to the patient's affected part while keeping a substantially parallel relation therebetween at the time of transplanting the cell sheet. Therefore, it is difficult to transplant the cell sheet to a desired position. Besides, since the deformation of the sheet supporting member is performed by use of a pneumatic pressure, it is necessary to prepare a pressure fluid supply source for supplying the pneumatic pressure. This leads to a complicated configuration including piping and the like, and to a complicated operation.

The disclosure here provides a cell culture transferring instrument which is rather simple in configuration and by which a sheet-shaped cell culture can be held relatively assuredly and easily and can be transferred to a desired position with high accuracy and without damaging the cell culture.

A cell culture transferring instrument for transferring a sheet-shaped cell culture, includes a body provided with a housing hole formed along an axial direction of the body, a displacement member which is inserted through the housing hole and is provided to be displaceable along the axial direction of the body, an adsorbent which is provided at a distal end of the displacement member, has flexibility, is capable of absorbing a liquid, and is capable of adsorbing the cell culture, and a supporting member which is formed from an elastic material, is provided between the adsorbent and the displacement member, and maintains the adsorbent in a predetermined shape, wherein the adsorbent is provided to be substantially orthogonal to the direction of displacement of the displacement member.

An adsorbent which has flexibility and can absorb liquids is provided at an end portion of a displacement member inserted through (positioned in) a housing section of a body, and a supporting member formed from an elastic material is provided between the adsorbent and the displacement member. In addition, the adsorbent is provided to be substantially orthogonal to the direction of displacement of the displacement member, and is maintained in a predetermined shape by the supporting member.

Therefore, when the displacement member is displaced in the axial direction to move the adsorbent toward the housing section side after a sheet-shaped cell culture is adsorbed by the adsorbent, the adsorbent is deformed against the elasticity of the supporting member, to be housed into the housing section. As a result, while adopting a simple configuration, the cell culture can be assuredly housed into the housing section of the body and can be transferred without being broken or damaged.

DETAILED DESCRIPTION

This cell culture transferring instrument 10, as shown in FIGS. 1 to 5, includes: a cylindrical body (body) 12 to be held by an operator (not shown in the drawing); a plunger (displacement member) 14 inserted through (positioned in) the interior of the cylindrical body 12; a plurality of supporting members 16 connected to a distal end 14a of the plunger 14; and an adsorbent 20 which is held by the supporting members 16 and is capable of adsorbing a sheet-shaped cell culture (cell culture) 18. Note that, in FIG. 1, the upper side of the cell culture transferring instrument 10 is referred to as the "proximal end" side (the direction of arrow A), and the lower side of the cell culture transferring instrument 10 as the "distal end" side (the direction of arrow B). This convention also applies to the other drawings.

The cylindrical body 12 is formed, for example, from a resin material in a hollow cylindrical shape such that the outer diameter is substantially constant along the axial direction (the direction of arrows A and B), and that a housing hole 22 is formed in the cylindrical body to pierce therethrough (and extends) along the axial direction (the direction of arrows A and B). The housing hole 22 is provided with a tapered section (guide section) 24 at its distal end portion, the tapered section (guide section) 24 gradually increasing in diameter toward the distal end portion. In other words, the housing hole 22 is so formed that its inside diameter approaches a maximum toward the distal end side (in the direction of arrow B).

The plunger 14 is composed of an elongated shaft body, is inserted through the housing hole 22 in the cylindrical body 12, is provided to be displaceable in the axial direction (the direction of arrows A and B), and is so provided that its proximal-most end 14b is always exposed by a predetermined length from the proximal end of the cylindrical body 12. Note that the plunger 14 is so provided that it is always displaced to the center of the housing hole 22 by guiding means (not shown in the drawing).

The supporting members 16 are formed, for example, from a superelastic alloy and are shaft-shaped (e.g., elongated). In addition, the supporting members 16 are arranged at regular spaced-apart angular intervals in a radial pattern, with the plunger 14 as a center of the radial pattern. Each supporting member 16 is connected at its one end portion to the distal end 14a of the plunger 14 substantially orthogonally. The other end portions of the supporting members 16 extend from the plunger 14 in such directions for gradually spacing away from one another. That is, the other end portions of the supporting members 16 extend radially outwardly from the plunger 14 and are arranged to form a substantially circular shape. Note that the plurality of the supporting members 16 are each substantially equal in length, and are each in a rectilinear shape. The supporting member 16 is, for example, formed by using a wire-shaped material as its core, or composed of a wire-shaped material itself. In this case, the wire-shaped material may extend from the supporting member 16 to the inside of the plunger 14.

The supporting member 16 is so provided that when a load is exerted on the supporting member 16, it is freely deformed elastically around its one end portion fixed to the plunger 14. When such a load is not exerted, the supporting member 16 is maintained in the rectilinear shape substantially orthogonal to the axis of the plunger 14 (see FIGS. 1 and 2). Note that the supporting member 16 may be turnably connected to the distal end 14a of the plunger 14.

The adsorbent 20 is formed, for example, from a cell culture adsorbing film having flexibility and hygroscopicity, such as a hydrophilic polyvinylidene fluoride (PVDF) film, in a circular disk shape having a predetermined thickness. The plurality of the supporting members 16 are adhered to one end face 20a of the adsorbent 20 that is located on the cylindrical body 12 side (oriented in the direction of arrow A). In other words, the adsorbent 20 is integrally linked to the plunger 14 through the plurality of supporting members 16. When the plunger 14 is displaced relative to the cylindrical body 12, the supporting members 16 and the adsorbent 20 are integrally displaced. In addition, when the supporting members 16 are elastically deformed, the adsorbent 20 is deformed integrally with, and following up to (corresponding to) the deformation of, the supporting members 16.

In addition, the other end face of the adsorbent 20 functions as an adsorbing surface 20b capable of adsorbing the sheet-shaped cell culture 18. Note that the one end face 20a and the other end face 20b of the adsorbent 20 are both formed in a planar shape.

The cell culture transferring instrument 10 according to the one embodiment is fundamentally configured as described above. Now, the operation and effects of the cell culture transferring instrument 10 will be described below. Note that the cell culture transferring instrument 10 is assumed to be in the state as shown in FIG. 1, wherein the adsorbent 20 is located on the outside of the distal end of the cylindrical body 12 and is maintained in a planar shape by the supporting members 16.

Figure 1:
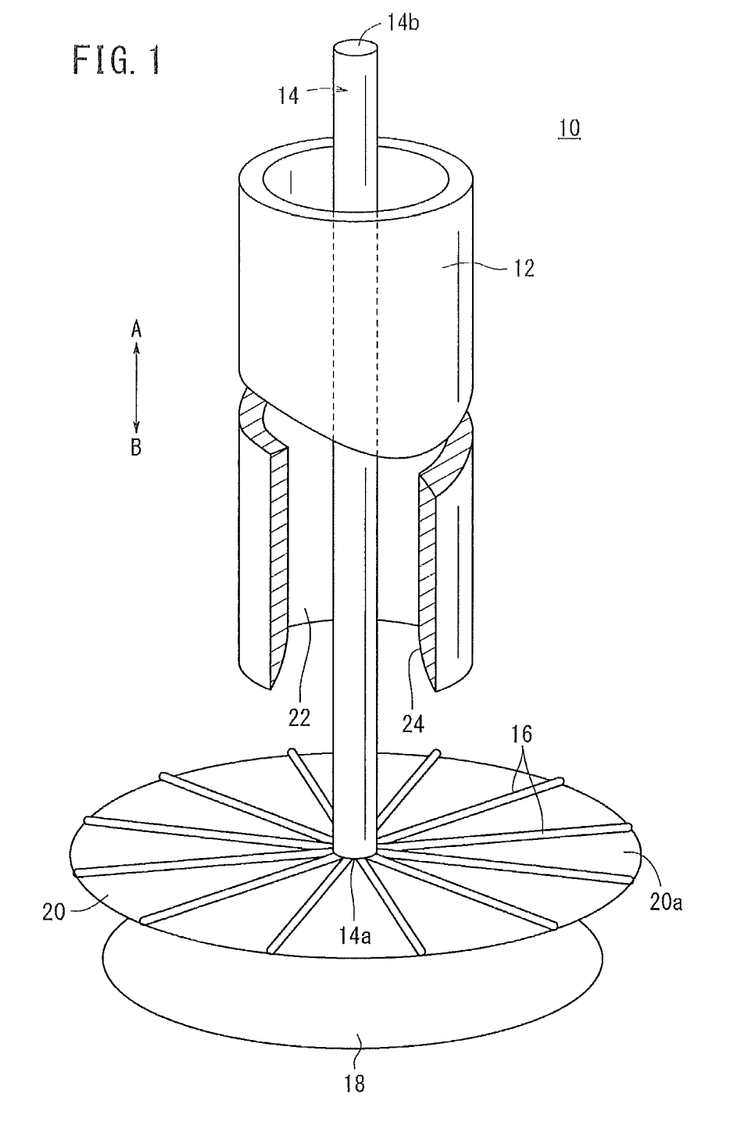
FIG. 1 is an external perspective view of a cell culture transferring instrument according to an embodiment.
Figure 2:
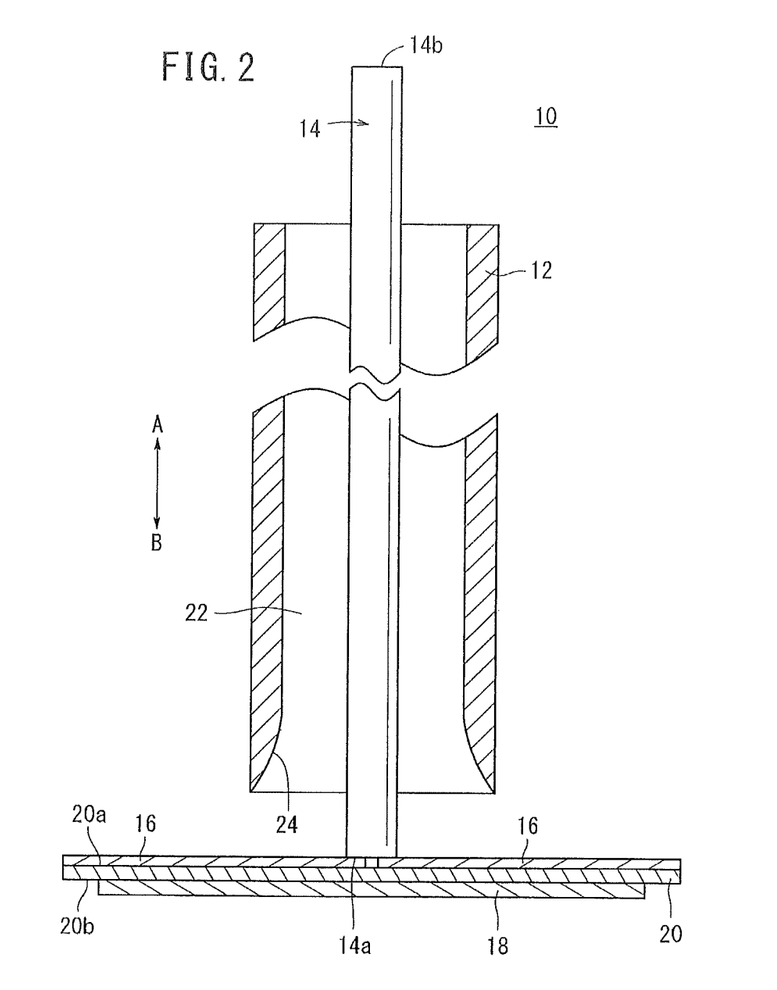
FIG. 2 is a longitudinal sectional view of the cell culture transferring instrument of FIG. 1, with a sheet-shaped cell culture adsorbed thereon.

First, as shown in FIG. 1, the sheet-shaped cell culture 18 cultivated in a culture dish (not shown) is prepared, and an operator (not shown), in the state of holding the cylindrical body 12, moves the cell culture transferring instrument 10 to the upper side of the sheet-shaped cell culture 18. Then, the adsorbent 20 of the cell culture transferring instrument 10 is set substantially in parallel to the sheet-shaped cell culture 18, and the adsorbent 20 is gradually lowered toward the sheet-shaped cell culture 18, thereby bringing the adsorbing surface 20b of the adsorbent 20 into contact with the sheet-shaped cell culture 18 (see FIG. 2). In this instance, for example, the diameter of the adsorbent 20 is set to be greater than the diameter of the sheet-shaped cell culture 18, as shown in FIG. 2, so that the sheet-shaped cell culture 18 is entirely covered by the adsorbent 20.

As a result, water in the sheet-shaped cell culture 18 is absorbed by the adsorbing surface 20b of the adsorbent 20 having hygroscopicity, and the sheet-shaped cell culture 18 is adsorbed onto the adsorbing surface 20b in the manner of being brought into secure contact with the adsorbing surface 20b.

Next, after confirming that the sheet-shaped cell culture 18 is adsorbed on the adsorbent 20 of the cell culture transferring instrument 10, the operator (not shown) raises the cell culture transferring instrument 10 in the direction (the direction of arrow A) for spacing (moving) away from the culture dish (not shown), and pulls the plunger 14 toward the proximal end 14b side (in the direction of arrow A) while holding the cylindrical body 12.

This ensures that the plunger 14 and the adsorbent 20 are displaced relative to the cylindrical body 12, and the adsorbent 20 with the sheet-shaped cell culture 18 adsorbed thereon is moved so as to approach the distal end of the cylindrical body 12. At the time of spacing (moving) the cell culture transferring instrument 10 away from the culture dish, the cell culture transferring instrument 10 is operated so that the adsorbent 20 with the sheet-shaped cell culture 18 adsorbed thereon will be slightly inclined relative to the surface of the culture dish (so that a little space will be formed between the surface of the culture dish and the adsorbent 20). This operation ensures that the sheet-shaped cell culture 18 does not peel from the adsorbent 20, and that preparation for transfer of the sheet-shaped cell culture 18 by the cell culture transferring instrument 10 is achieved.

Figure 3:
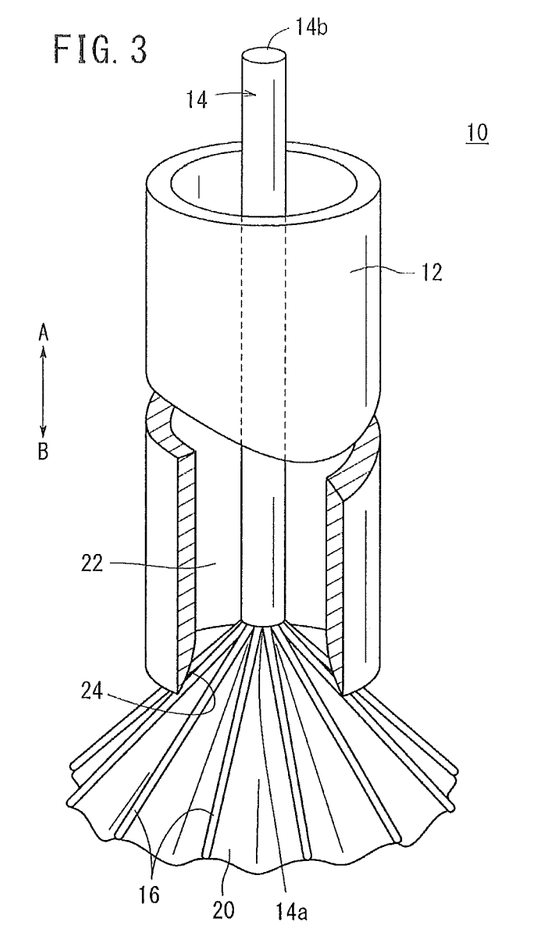
FIG. 3 is an external perspective view showing a state in which the sheet-shaped cell culture has started being housed into the inside of a cylindrical body by the cell culture transferring instrument of FIG. 1.
Figure 4:
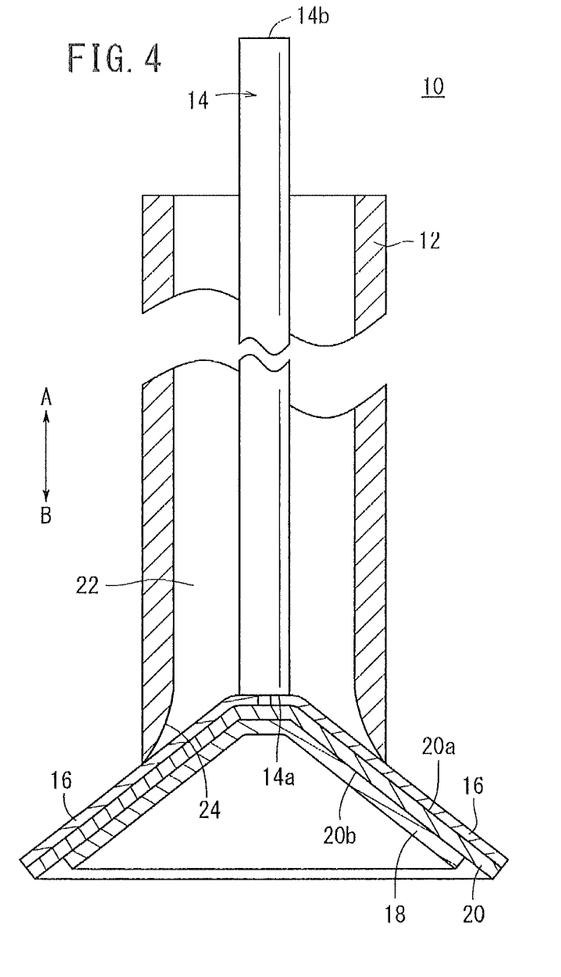
FIG. 4 is a longitudinal sectional view of the cell culture transferring instrument shown in FIG. 3.

Then, with the distal end 14a of the plunger 14 housed into (positioned in) the distal end of the cylindrical body 12, the plurality of supporting members 16 are brought into contact with the distal end of the cylindrical body 12. Furthermore, with the plunger 14 pulled toward the proximal end 14b side (in the direction of arrow A), the supporting members 16 orthogonal to the axis of the cylindrical body 12, under the action of contact with the distal end, are tilted around their one end portions connected to the plunger 14, in such directions that the other end portions of the supporting members 16 are spaced farther away from the distal end (in the direction of arrow B), as shown in FIGS. 3 and 4. Thus, the adsorbent 20, to which the supporting members 16 are adhered and on which the sheet-shaped cell culture 18 is adsorbed, follows up to (is folded along with) the tilting of the supporting members 16, thereby being gradually folded to become substantially conical in sectional shape.

In other words, as a result of the elastic deformation of the supporting members 16, the adsorbent 20 and the sheet-shaped cell culture 18 adsorbed on the inside of the adsorbent 20 are brought into a tapered shape, which is tapered off toward the plunger 14 side (in the direction of arrow A).

Furthermore, with the plunger 14 pulled toward the proximal end 14b side (in the direction of arrow A), the supporting members 16, having been elastically deformed and inclined, come into contact with the tapered section 24 of the housing hole 22. Then, under the force pulling the plunger 14 upward (in the direction of arrow A), the supporting members 16 are further tilted around their one end portions because of the tapered section 24, against the elastic force. Moreover, the adsorbent 20 adhered to the supporting members 16 and the sheet-shaped cell culture 18 adsorbed on the adsorbent 20 are also deformed in the manner of being gradually folded, to be gradually decreased in outside diameter and to be thereby progressively housed into (positioned in) the interior of the housing hole 22, as shown in FIG. 5.

Figure 5:
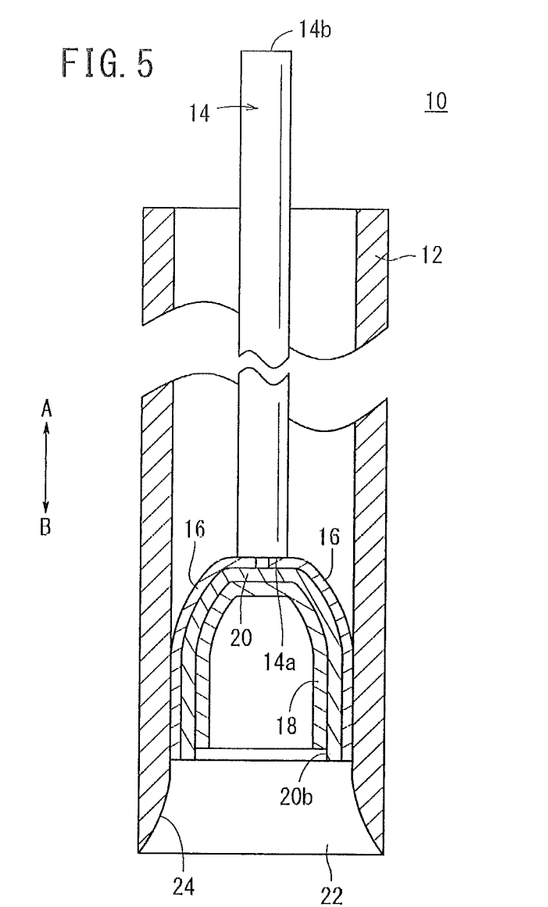
FIG. 5 is a sectional view showing a state in which the sheet-shaped cell culture has been completely housed into the cylindrical body of the cell culture transferring instrument of FIG. 4.

Then, as shown in FIG. 5, because of the displacement of the plunger 14 toward the proximal end 14b side (in the direction of arrow A), the other end portions of the supporting members 16 are completely housed into the housing hole 22. Simultaneously, the outer edge portions of the adsorbent 20 and the sheet-shaped cell culture 18 are folded in a manner such that the diameter of the adsorbent 20 and shaped cell culture 18 is further decreased, and they are housed in the interior of the housing hole 22.

In the state where the sheet-shaped cell culture 18 is thus housed in the interior of the cylindrical body 12, the operator (not shown) moves the cell culture transferring instrument 10 into the vicinity of the patient's affected part. As illustrated in FIG. 5, the cell culture and the adsorbent positing in the housing hole possess an upside-down U-shape (concave-shaped) in cross-section.

Next, the cell culture transferring instrument 10 is so disposed that the cylindrical body 12 faces the patient's affected part and the cylindrical body 12 is substantially orthogonal to the affected part, after which the cell culture transferring instrument 10 is gradually lowered to dispose (position) the distal end of the cylindrical body 12 at a position of a predetermined spacing from the affected part. Access to the patient's affected part can, for example, be made by introducing the cell culture transferring instrument 10 into the inside of the living body via an incision made in the patient's body surface, and bringing the distal end of the cell culture transferring instrument 10 close to the surface of the heart or the like that is the target part. In this instance, since the sheet-shaped cell culture 18 is housed inside the cylindrical body 12, the transfer can be prevented from being obstructed by the access to the affected part. At the time of accessing the patient's affected part, the procedure can be carried out by use of an endoscope.

Then, with the cylindrical body 12 fixed, the operator slowly pushes the plunger 14 again downward (in the direction of arrow B), whereby the adsorbent 20 and the sheet-shaped cell culture 18 having been housed in the housing hole 22 of the cylindrical body 12 are pushed out of the housing hole 22 to the outside. This ensures that the adsorbent 20 starts being gradually increased in diameter radially outward together with the sheet-shaped cell culture 18 adsorbed on the inside thereof, in the state of being located near the tapered section 24 of the cylindrical body 12, under the elastic force of the supporting members 16. Then, the adsorbent 20 is moved to the outside of the cylindrical body 12 together with the sheet-shaped cell culture 18, to be thereby returned into the planar shape under the elastic force.

Finally, the cell culture transferring instrument 10 is again lowered slowly, to bring the sheet-shaped cell culture 18 adsorbed on the adsorbent 20 into contact with the affected part. This results in the sheet-shaped cell culture 18 being adsorbed onto and transplanted (adhered) to the affected part by the affected part's water content or the like.

Note that the sheet-shaped cell culture 18 shows a stronger adsorbing force on its other end face (the side of transplantation to the affected part) than on its one end face (which is adsorbed on the adsorbent 20), so that the sheet-shaped cell culture 18 can be easily separated from the adsorbent 20 by bringing the other end face into contact with the affected part. Then, the cell culture transferring instrument 10 is spaced (moved) away from the affected part, whereby transfer of the sheet-shaped cell culture 18 to the patient's affected part is completed.

Thus, in this embodiment, the adsorbent 20 having flexibility and hygroscopicity is connected to the distal end 14a of the plunger 14 through the plurality of elastically deformable supporting members 16. In addition, at the time of adsorption of the sheet-shaped cell culture 18 by the adsorbent 20, the adsorbent 20 can be maintained in the planar shape by the supporting members 16. This ensures that by pulling the adsorbent 20 into the interior of the cylindrical body 12 through the plunger 14 after the adsorption of the sheet-shaped cell culture 18 by the adsorbent 20, the adsorbent 20 and the sheet-shaped cell culture 18 can be deformed together with the supporting members 16 and be thereby housed into the housing hole 22.

In other words, while adopting such a simple configuration, the sheet-shaped cell culture 18 can be assuredly held and be transferred without being broken or damaged.

In addition, the sheet-shaped cell culture 18 transferred in the state of being housed in (positioned in) the cylindrical body 12 can be assuredly transplanted to a desired position of the patient's affected part for the reason as follows. Specifically, at a desired position facing the affected part, the plunger 14 is displaced relative to the cylindrical body 12, so as to push out the adsorbent 20 housed in the cylindrical body 12 to the outside, whereby the adsorbent 20 and the sheet-shaped cell culture 18 can be returned into the planar shape assuredly and suitably.

Furthermore, the adsorbent 20 is configured to be substantially orthogonal to the axial direction (the direction of arrows A and B) of the cylindrical body 12 and the plunger 14. Therefore, at the time when the sheet-shaped cell culture 18 adsorbed by the adsorbent 20 is transplanted to the affected part, the procedure can be carried out by moving the cylindrical body 12 toward and away from the affected part in a perpendicular relationship. As a result, the sheet-shaped cell culture 18 can be easily positioned into the desired position on the affected part, and the transplantation can be performed easily and with high accuracy.

Note that a configuration wherein the adsorbent 20 (together with the sheet-shaped cell culture 18) can be housed through deformation by being gradually pulled into the housing hole 22 by the plunger 14 after the adsorbent 20 comes into contact with the distal end of the cylindrical body 12 is adopted in the aforementioned embodiment, but this configuration is not restrictive. For instance, a configuration may be adopted where when predetermined conditions (a lapse of time, a variation in temperature, or the like) are satisfied after adsorption of the sheet-shaped cell culture 18 and before the sheet-shaped cell culture 18 is adsorbed by the adsorbent 20 and housed into the cylindrical body 12, the supporting members 16 are tilted relative to the plunger 14, which is attended by preliminary deformation of the adsorbent 20 and the sheet-shaped cell culture 18 into a size for enabling them to be housed into the aforesaid housing hole 22. This configuration ensures that the intended housing can be achieved even with a small force for pulling in the plunger 14 toward the proximal end 14*b* side (in the direction of arrow A).

The detailed description above describes an embodiment of a cell culture transferring instrument representing one example of the cell culture transferring instrument disclosed here. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of transferring a cell culture using a cell culture transferring instrument, the cell culture transferring instrument comprising a hollow body possessing a distal-most end, a displacement member movably positioned in the hollow body, an adsorbent fixed at a distal end of the displacement member, and a supporting member positioned on the adsorbent to maintain a shape of the adsorbent, the method comprising:

axially moving the displacement member towards the cell culture to bring the adsorbent and the cell culture into contact with one another when the distal end of the displacement member extends distally beyond the distal-most end of the hollow body and the adsorbent is outside the hollow body;

axially moving the displacement member and the cell culture attached to the adsorbent to move the cell culture to a position inside the hollow body, the hollow body maintaining the adsorbent and the cell culture in a first shape;

positioning the hollow body adjacent to an affected part of a living body;

axially moving the displacement member and the cell culture attached to the adsorbent to position the cell culture outside the hollow body, the adsorbent and the cell culture taking a second shape different from the first shape;

contacting the affected part of the living body with the cell culture such that the cell culture sticks to the affected part of the living body; and moving the displacement member away from the cell culture while the cell culture remains stuck to the affected part of the living body.

2. The method according to claim 1, wherein the axial movement of the displacement member and the cell culture attached to the adsorbent to position the cell culture inside the hollow body causes the cell culture to have a concave-shaped cross-section.

3. The method according to claim 1, wherein the axial movement of the displacement member and the cell culture attached to the adsorbent to position the cell culture inside the hollow body causes both the adsorbent and the cell culture to have a concave-shaped cross-section.

4. The method according to claim 1, wherein the adsorbent is a cell culture adsorbing film having flexibility and hygroscopicity.

5. The method according to claim 1, further comprising: maintaining the adsorbent and the cell culture in a substantially planar shape while axially moving the displacement member and the cell culture towards the inside of the hollow body, the cell culture and the adsorbent being maintained in the substantially planar shape by the supporting member.

* * * * *